United States Patent [19]

Horowitz et al.

[11] Patent Number: 4,683,007
[45] Date of Patent: Jul. 28, 1987

[54] TITANIUM DIOXIDE DISPERSIONS AND PROCESSES FOR THEIR PRODUCTION

[75] Inventors: Carl Horowitz, Brooklyn; John M. Ryan, Woodhaven; Mohan L. Sanduja, Flushing, all of N.Y.; Kenneth K. Sugathan, Piscataway, N.J.; Paulose P. Thottathil, Brooklyn, N.Y.

[73] Assignee: Forsythe Cosmetic Group, Ltd., Lawrence, N.Y.

[21] Appl. No.: 748,692

[30] Foreign Application Priority Data

Jan. 29, 1985 [SE] Sweden ............................. 8200500

[22] Filed: Jun. 25, 1985
[51] Int. Cl.$^4$ ................................. C09C 1/36
[52] U.S. Cl. ..................... 106/308 M; 106/195; 106/299; 106/300; 527/313; 527/314
[58] Field of Search ............... 527/314, 313; 106/178, 106/193 J, 193 P, 195, 300, 299, 308 M

[56] References Cited

U.S. PATENT DOCUMENTS 2,602,756  7/1952  Hucks ................................. 106/193
3,673,135  6/1972  Blake et al. ......................... 527/314
4,435,531  3/1984  Nakayama et al. ................... 524/37

OTHER PUBLICATIONS

Derwent Abstract Accession No. 73-38502U/27, Japanese Patent No. J73014772-B.
Chemical Abstract, vol. 80, No. 135037m, Japanese Patent No. 73/45527, Jun. 29, 1973.

*Primary Examiner*—Amelia B. Yarbrough
*Attorney, Agent, or Firm*—Lee C. Robinson, Jr.

[57] ABSTRACT

Dispersions of titanium dioxide pigments with improved long-term resistance to pigment settling and precipitation are disclosed. The pigment dispersions are formed by chemically grafting vinyl and/or acrylic polymers to nitrocellulose in dispersions of nitrocellulose and titanium dioxide pigments. Nitrocellulose forms a loose association with titanium dioxide in dispersion. The chemical grafting improves the precipitation and settling resistance of nitrocellulose, and thus the precipitation and settling resistance of the associated titanium dioxide.

14 Claims, No Drawings

TITANIUM DIOXIDE DISPERSIONS AND PROCESSES FOR THEIR PRODUCTION

BACKGROUND OF THE INVENTION

This invention relates to improved dispersions of titanium dioxide pigments such as commercial nail polishes.

One of the main problems associated with most titanium dioxide dispersions available on the market is their instability over a period of time. It is a common phenomenon to find dispersions contained in a bottle separated into two phases. One of the phases, in a particulate form, tends to settle at the bottom and sides of the bottle. This is because of the separation or precipitation of a pigment material like titanium dioxide from the rest of the matrix of the formulation. The time period for this precipitation of titanium dioxide or similar pigment material varies from a few weeks to a few months. Nail polishes whose titanium dioxide pigments are unstable in dispersion often show insufficient flexibility, hardness, and gloss. Excessive brittleness and chipping characteristics are also frequent.

Industries dealing with titanium dioxide products, like nail polish, are plagued by a gradual decrease in the quality and value of their products with time. Because the problem continues when the product is in the hands of consumers, bulk sales of large quantities of the product is less practicable than it could otherwise be. Shelf life of the products in the hands of retailers is similarly limited.

SUMMARY

It is accordingly an object of the present invention to provide improved long term stability to nail polishes and other titanium dioxide products. This is done by increasing the stability of the dispersion so that precipitation or settling of the pigments does not readily occur.

It is another object of the present invention to provide improved characteristics of titanium dioxide nail polishes such that they have good flexibility, hardness, gloss and abrasion resistance.

It is a further object of the invention to provide a nail polish with reduced incidence of chipping and flaking when applied to the nail.

Still another object of the invention is to provide a new and improved nail polish that is economical to manufacture and thoroughly reliable in use.

DESCRIPTION OF CERTAIN PREFERRED EMBODIMENTS

Although the specific examples of the invention shown herein relate to nail polish preparation, the invention is broadly applicable to related products comprised of titanium dioxide as one of the pigments in dispersion. A starting solution is used of titanium dioxide and nitrocellulose. Both compounds are present in nearly all commercial nail polishes. For titanium dioxide products which do not generally require nitrocellulose, nitrocellulose is added as a first step. Titanium dioxide naturally forms a loose association with nitrocellulose in solution.

Compositions and processes in accordance with the present invention provide increased dispersion stability and precipitation resistance of titanium dioxide by improving the dispersion stability and precipitation resistance of the nitrocellulose molecules to which titanium dioxide molecules are loosely associated. Alternative embodiments allow for the introduction of titanium dioxide after nitrocellulose has already been stabilized in accordance with the instant invention. Hence the starting material (hereinafter "substrate") of the invention may be either nitrocellulose dispersions or dispersions of a nitrocellulose-titanium dioxide complex. Improving the solubility of the substrate is achieved by grafting vinyl and/or acrylic monomers to the substrate through the free hydroxyl group of the nitrocellulose molecule. As a first step to grafting, a substrate radical is formed by removal of the hydrogen from the hydroxyl group by a graft initiator (represented in the reaction steps below as "GI") such as silver perchlorate or ferrous sulfate. A typical reaction step by which the radical is formed is set forth below as step 1:

1. $TiO_2-OC_6H_7(ONO_2)_2OH + GI \rightarrow TiO_2-OC_6H_7(ONO_2)_2O + H^+ + GI^-$ The resulting radical then reacts with vinyl and/or acrylic monomers which have been added to initiate and propagate graft polymerization. Monomers which may be used include but are not limited to hydroxyethyl methacrylate, butyl methacrylate, methyl methacrylate, and gamma-methacryloxypropyl trimethoxysilane. Typical initiation and propagation steps of the graft polymerization are set forth below as steps 2 and 3 respectively:

2. 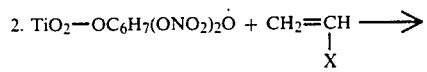

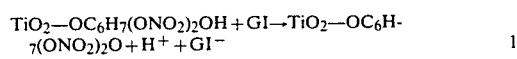

3. 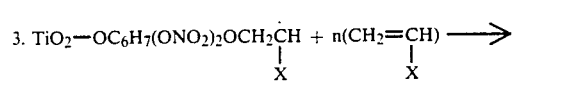

where X is either —OR or

and where R is allyl, phenyl, or alkyl, said alkyl typically being of from 1 to 10 carbon atoms.

All of the foregoing reactions take place in the presence of a peroxide which concurrently regenerates the graft initiator forming a free radical as shown in the reaction below:

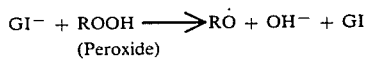
(Peroxide)

Where R is allyl, phenyl, or alkyl, said alkyl typically being of from 1 to 10 carbon atoms.

The graft propagation shown in Step 3 may be terminated by radical combination which may occur in one of two ways. Step 4, set forth below, shows the final product when termination is a result of a combination of one of the free radicals with one of the polymerized substrate radicals. Step 4' shows the product when termination is caused by combination of two polymerized substrate radicals. The final product of both steps 4 and 4' are dispersions which are very resistent to precipitation:

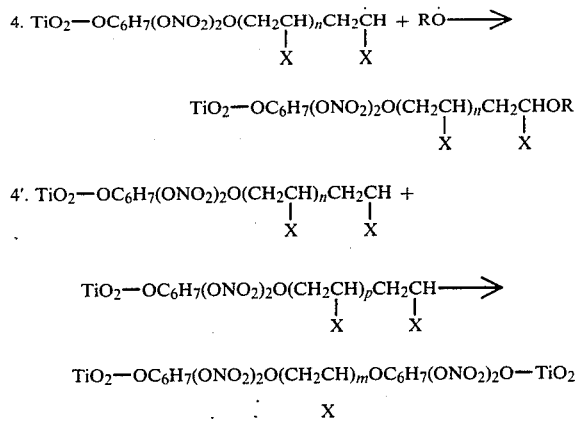

Where $m = n + p + 2$, where m, n and p are positive integers, and where m is usually, in the range between 1000 and 2000.

When nitrocellulose grafted to vinyl and/or acrylic polymers is used in commercial nail polishes, the increased dispersion stability of titanium dioxide enhances a number of other important qualities. Nail polishes so treated show good adhesion and flexibility while maintaining exceptional gloss and hardness. Also chipping and flaking of the polish after it has been applied to a nail are reduced. Shown below is test data from experiments performed on nail lacquer treated with the compounds disclosed by the instant invention.

TEST DATA

1. STABILITY

Ten to 15 grams of nail polish was taken in centrifuge tubes and subjected to centrifugation for 20 minutes at a speed of 7000 rpm using IEC CLINICAL CENTRIFUGE. On visual inspection, there did not appear to be separation of titanium dioxide particulate from the matrix of suspension.

2. THERMAL STABILITY

Ten to 15 grams of nail polish formulation was taken in a test tube and subjected to heat treatment in warm water (180° F.) for 2 hours. During the process of heating as well as on cooling the test tube to room temperature, there was no separation or settling out of titanium dioxide from the suspension.

3. ADHESION

Nail polish was uniformly applied onto a glass slide and air cured subsequently by keeping it at room temperature for 30 minutes. A cross-hatch pattern was scribed on the coated surface with a sharp blade. A piece of ordinary ¾ in. cellophane tape—several inches long—was applied over the entire surface of the cross-hatched pattern, making sure that a tab large enough to be grasped firmly with the fingers was left well above the pattern. The tape was then removed by pulling rapidly and evenly toward the bottom of the test slab. On visual inspection, there was no removal of coating from the scribed area.

4. FLEXIBILITY

A polyester film was coated with nail polish and the coated film was twisted through 180° angle. There was no cracking or flaking of the coat on the film surface.

EXAMPLES

Shown below are some specific examples representing preferred embodiments of the invention. Each example merely illustrates the invention and is not intended to impose any limitation upon the scope of the invention.

Example 1

Additive Base

An additive base for use in treating colored nail polishes is prepared by introducing the following compounds to a reaction vessel in the order listed and in the relative amounts by weight as shown below. Each compound is added with constant mechanical stirring. No new compound is introduced until stirring accomplishes a uniform mix of all prior compounds:

| Compound | Parts by Weight |
|---|---|
| N—Butyl Acetate | 284.00 |
| Nitrocellulose R.S. ½ sec. | 200.00 |
| Ethyl Acetate | 150.00 |
| Toluene | 140.00 |
| Isopropanol (IPA) | 86.00 |
| Santolite MHP (Toluene Sulfonamide Formaldehyde) | 80.00 |
| Dibutyl Phthalate (DBP) | 33.00 |
| Camphor | 7.00 |
| Bentone Chips | 80.00 |
| Prepolymer Acryloid F-10 (Polybutyl methacrylate, 40% solutions in mineral spirits) | 20.00 |
| 10% Phosphoric Acid in Butyl Acetate | 5.00 |
| Isobutyl Acetate | 100.00 |
| Silane A174 (gamma-methacryloxypropyl-trimethoxysilane) | 0.50 |
| Methyl Methacrylate | 0.50 |
| Ferrous Sulfate | 0.0005 |
| Benzoyl Peroxide (10% solution in MEK) | 0.50 |

Example 2

Additive Base

An additive is prepared as in Example 1 wherein the compounds and relative parts by weight are as shown below:

| Compound | Parts by Weight |
|---|---|
| Nitrocellulose R.S. ½ sec. | 15.00 |
| Santolite MHP (Toluene sulfonamide formaldelyde) | 7.50 |
| Dibutyl Phthalate | 3.75 |
| N—Butyl Acetate | 29.35 |
| Ethyl Alcohol | 6.40 |
| Ethyl Acetate | 1.10 |
| Toluene | 36.90 |
| Bentone Chips | 5.00 |
| Acryloid F.10 (Polybutyl methacrylate, 40% in mineral spirits) | 5.00 |
| 10% Phosphoric Acid Solution in Butyl Acetate | 1.00 |
| Disperse Ayd #1 | 1.00 |
| Triton X-100 (Octyl Phenoxy polyethoxy ethanol) | 0.50 |
| Silane A174 (gamma-Methacryloxypropyltrimethoxysilane | 0.1 |
| Ferrous Sulfate | 0.0001 |

Example 3

Additive Base

An additive is prepared as in Example 1 wherein the compounds and relative parts by weight are as shown below:

| Compound | Parts by Weight |
| --- | --- |
| Nitrocellulose R.S. ½ sec. | 16.00 |
| Santolite MS.80 (Toluene sulfonamide formaldehyde, 80% solutions in butyl acetate) | 8.00 |
| Dibutyl Phthalate | 3.00 |
| Camphor | 0.50 |
| N—Butyl Acetate | 16.24 |
| Ethyl Acetate | 13.15 |
| Isopropyl Alcohol | 6.85 |
| Toluene | 36.00 |
| Bentone Chips | 5.00 |
| Acryloid F.10 (Polybutyl methacrylate, 40% solution in mineral spirits) | 1.00 |
| Acryloid A101 (Polymethyl methacrylate, 40% solution in methylethyl ketone) | 1.00 |
| 10% Phosphoric Acid Solution in Butyl Acetate | 0.50 |
| Disperse Ayd #1 | 1.00 |
| Triton X-45 (Octyl phenoxy-polyethoxy ethanol) | 0.50 |
| Methyl Methacrylate | 0.20 |
| Ferrous Sulfate | 0.0002 |
| Benzoyl Peroxide (10% in MEK) | 0.10 |

Example 4

Additive Base

An additive is prepared as in Example 1 wherein the compounds and relative parts by weight are as shown below:

| Compound | Parts by Weight |
| --- | --- |
| Nitrocellulose R.S. ½ sec. | 15.00 |
| Santolite MS.80 (Toluene sulfonamide formaldehyde, 80% solution in butyl acetate) | 5.20 |
| Santolite MHP (Aryl sulfonamide formaldehyde) | 2.80 |
| Dibutyl Phthalate | 3.00 |
| Camphor | 0.75 |
| N—Butyl Acetate | 28.25 |
| Ethyl Acetate | 8.00 |
| Isopropyl Alcohol | 6.50 |
| Bentone Chips | 5.00 |
| M.P.A. 60 | 0.50 |
| Disperse Ayd #1 | 1.00 |
| Triton X-45 (Octyl phenoxy-polyethoxyethanol) | 0.50 |
| Orthophosphoric Acid | 0.02 |
| Acryloid F.10 (Polybutyl methacrylate, 40% in mineral spirits) | 4.50 |
| Silane A174 (Gamma-Methacryloxy propyltrimethoxy silane) | 0.20 |
| Methyl Methacrylate | 0.15 |
| Ferrous Sulfate | 0.00015 |
| Benzoyl Peroxide (10% in MEK) | 0.10 |

Example 5

Additive Base

An additive is prepared as in Example 1 wherein the compounds and relative parts by weight are as shown below:

| Compound | Parts by Weight |
| --- | --- |
| Nitrocellulose R.S. ½ sec. | 16.00 |
| Toluene | 36.34 |
| Ethyl Acetate | 25.56 |
| Santolite MHP (Tolenesulfonamide formaldehyde) | 8.00 |
| Santiciser 8 (n, ethyl O,P - toluene sulfonamides) | 3.00 |
| Camphor | 0.50 |
| N—Butyl Acetate | 5.00 |
| Isopropanol | 2.00 |
| Bentone Chips | 5.00 |
| MPA. 60 | 0.30 |
| Disperse Ayd #1 | 1.00 |
| Triton X-45 (Octyl phenoxy polyethoxy ethanol) | 0.20 |
| Triton X-100 (Octyl phenoxy polyethoxy ethanol) | 0.30 |
| Orthophosphoric Acid | 0.02 |
| Acryloid A101 (Polymethyl methacrylate, 40% solution in methyl ethyl ketone) | 2.00 |
| Hydroxyethyl Methacrylate | 0.20 |
| Ferrous Sulfate | 0.0002 |
| Benzoyl Peroxide (10% in MEK) | 0.10 |

Example 6

Clear Additive

A clear additive for use in modifying clear nail polishes is prepared by addition of the following compounds in the order they appear below and in the relative parts by weight as shown. The mixture is constantly subjected to stirring with a mechanical stirrer. No new compound is added until a uniform mixture of prior compounds is obtained:

| Compound | Parts by Weight |
| --- | --- |
| Prepolymer Acryloid F-10 (Polybutyl methacrylate, 40% solution in mineral spirits) | 40.00 |
| Perenol S-4 | 4.00 |
| Acetone | 1.00 |
| Monomer Silane A-174 (gamma-Methacryloxypropyl trimethoxy silane) | 0.10 |
| Ferrous Sulfate | 0.0001 |
| Benzoyl Peroxide (10% in MEK) | 0.05 |

Example 7

Clear Additive

A clear additive is prepared as in Example 6 whereby the compounds and relative parts by weight are as follows:

| Compound | Parts by Weight |
| --- | --- |
| Prepolymer Acryloid A101 (Polymethyl methacrylate, 40% solutions in methylethyl ketone) | 30.00 |
| Perenol S-4 | 4.00 |
| Toluene | 11.00 |
| Silane A174 (gamma-methacryloxy | 0.10 |

(-continued from previous page)

| Compound | Parts by Weight |
| --- | --- |
| Benzoyl Peroxide (10% solution in MEK) | 0.2 |

Example 8
Clear Additive

A clear additive is prepared as in Example 6 whereby the compounds and relative parts by weight are as follows:

| Compound | Parts by Weight |
| --- | --- |
| Prepolymer Acryloid F-10 (Poly-butyl methacrylate, 40% solution in mineral spirits) | 40.00 |
| Perenol S-4 | 4.00 |
| Toluene | 1.00 |
| Methyl Methacrylate | 0.10 |
| Ferrous Sulfate | 0.0001 |
| Benzoyl Peroxide (10% in MEK) | 0.50 |

Example 9
Clear Additive

A clear additive is prepared as in Example 6 whereby the compounds and relative parts by weight are as follows:

| Compound | Parts by Weight |
| --- | --- |
| Prepolymer Acryloid F-10 (Poly-butyl methacrylate, 40% solution in mineral spirits) | 30.00 |
| Acryloid A101 polymethyl methacrylate, 40% solution in methyl ethyl ketone) | 5.00 |
| Perenol S-4 | 5.00 |
| Acetone | 5.00 |
| Hydroxy ethyl Methacrylate | 0.10 |
| Ferrous Sulfate | 0.0001 |
| Benzoyl Peroxide (10% in MEK) | 0.05 |

EXAMPLE 10
Clear Additive

A clear additive is prepared as in Example 6 whereby the compounds and relative parts by weight are as follows:

| Compound | Parts by Weight |
| --- | --- |
| Prepolymer Acryloid A101 (polymethyl methocrylate, 40% solution in methyl ethyl ketone) | 20.00 |
| Prepolymer Acryloid F-10 | 12.00 |
| Perenol S-4 | 5.00 |
| Toluene | 8.00 |
| Silane A187 (gamma glycidoxy-propyltrimethoxy silane) | 0.10 |
| Ferrous Sulfate | 0.0001 |
| Benzoyl Peroxide (10% in MEK) | 0.05 |

-continued

| Compound | Parts by Weight |
| --- | --- |
| propyltrimethoxysilane) | |
| Ferrous Sulfate | 0.0001 |
| Benzoyl Peroxide (10% in MEK) | 0.05 |

The terms, expressions, compounds, and relative quantities of compounds discussed in the examples above are used as terms of description only and not as terms of limitation. There is no intention in the use of such terms, expressions, compounds or relative quantities of excluding any equivalents or portions thereof, it being recognized that various modifications are possible within the scope of the invention.

We claim:

1. A stable dispersion comprising: (1) titanium dioxide; and (2) nitrocellulose grafted directly to a polymer or copolymer consisting of monomers of the formula $$CH_2{=}CY$$
$$|$$
$$X$$

wherein Y is $CH_3$ or H and X is

or —OR, and R is alkyl, allyl or phenyl.

2. A process for preparing a stable dispersion for use as a lacquer, which comprises: (1) preparing a dispersion of nitrocellulose; (2) contacting the dispersion with one or more of the monomers selected from the group consisting of $$CH_2{=}CY$$
$$|$$
$$X$$

wherein Y is $CH_3$ or H and X is

or —OR, and R is alkyl, allyl or phenyl; (3) initiating graft polymerization of the monomer directly onto the nitrocellulose through a free hydroxyl group of the nitrocellulose; and (4) adding titanium dioxide to the resulting dispersion.

3. A process for preparing a stable dispersion for use as a lacquer, which comprises: (1) preparing a dispersion of nitrocellulose and titanium dioxide; (2) contacting the dispersion with one or more of the monomers selected from the group consisting of $$CH_2{=}CY$$
$$|$$
$$X$$

wherein Y is $CH_3$ or H and X is

or —OR, and R is alkyl, allyl or phenyl; and (3) initiating graft polymerization of the monomer directly onto the nitrocellulose through a free hydroxyl group of the nitrocellulose.

4. A process as in claim 2 wherein grafting takes place in the presence of a peroxide.

5. A process as in claim 2 wherein silver perchlorate or ferrous sulfate is used as a graft initiator.

6. A process as in claim 2 wherein grafting takes place in the presence of a peroxide, and wherein silver perchlorate or ferrous sulfate is used as a graft initiator.

7. A process as in claim 2, wherein the monomer is selected from the group consisting of hydroxyethyl methacrylate, butyl methacrylate, methyl methacrylate, and gamma-methacryloxypropyl trimethoxysilane, wherein grafting takes place in the presence of a peroxide, and wherein silver perchlorate or ferrous sulfate is used as a graft initiator.

8. A process as in claim 3 wherein grafting takes place in the presence of a peroxide.

9. A process as in claim 3 wherein silver perchlorate of ferrous sulfate is used as a graft initiator.

10. A process as in claim 3 wherein grafting takes place in the presence of a peroxide and wherein silver perchlorate or ferrous sulfate is used as a graft initiator.

11. A process as in claim 3, wherein grafting takes place in the presence of a peroxide; silver perchlorate or ferrous sulfate is used as a graft initiator; and the monomer is selected from the group consisting of hydroxyethyl methacrylate, butyl methacrylate, methyl methacrylate, and gamma-methacryloxypropyl trimethyoxysilane.

12. A stable dispersion as in claim 1, wherein the polymer or copolymer consists essentially of monomers which may be the same or different and which are selected from the group consisting of hydroxyethyl methacrylate, butyl methacrylate, methyl methacrylate, and gamma-methacryloxypropyl trimethylsilane.

13. A process as in claim 2, wherein the monomer is selected from the group consisting of hydroxyethyl methacrylate, butyl methacrylate, methyl methacrylate, and gamma-methacryloxypropyl trimethoxysilane.

14. A process as in claim 3, wherein the monomer is selected from the group consisting of hydroxyethyl methacrylate, butyl methacrylate, methyl methacrylate, and gamma-methacryloxypropyl trimethoxysilane.

* * * * *